United States Patent [19]

Kuhl et al.

[11] Patent Number: 4,832,021

[45] Date of Patent: May 23, 1989

[54] APPARATUS AND METHOD FOR ASSEMBLY AND DISASSEMBLY OF INTERCHANGEABLE SURGICAL ACOUSTIC MEMBERS

[75] Inventors: Peter Kuhl, Jackson Heights; Alan Broadwin, Brooklyn, both of N.Y.; Robert W. Hornlein, Stamford, Conn.

[73] Assignee: Cooper LaserSonics, Inc., Santa Clara, Calif.

[21] Appl. No.: 115,623

[22] Filed: Oct. 30, 1987

Related U.S. Application Data

[63] Continuation of Ser. No. 782,306, Oct. 1, 1985, abandoned, which is a continuation-in-part of Ser. No. 761,495, Aug. 1, 1985, abandoned.

[51] Int. Cl.$^4$ .............................................. A61B 17/00
[52] U.S. Cl. ................................. 128/303 R; 81/467; 81/59.1; 269/287
[58] Field of Search ................... 81/59.1, 124.4, 124.5, 81/125.1, 467, 473, 478, 474; 267/287, 309, 328; 128/1 R, 303 R

[56] References Cited

U.S. PATENT DOCUMENTS

| 37,865 | 3/1863 | Griswold | 81/125.1 |
|---|---|---|---|
| 870,151 | 10/1906 | Abell | 81/59.1 |
| 1,186,135 | 6/1916 | Rowe | 269/287 |
| 1,410,032 | 5/1921 | Palmer | 81/124.4 |
| 2,482,387 | 9/1949 | Veneman | 81/52.4 |
| 2,502,587 | 7/1946 | Phipps | 81/124.4 |
| 2,512,032 | 6/1950 | Mellert | 81/52.5 |
| 3,589,363 | 6/1971 | Banko | 128/276 |
| 3,927,582 | 12/1975 | Hertelendy | 81/58.2 |
| 4,270,417 | 6/1981 | Tesoro | 81/62 |
| 4,403,530 | 9/1983 | Biddle | 81/478 |

FOREIGN PATENT DOCUMENTS

| 732738 | 2/1943 | Fed. Rep. of Germany | 81/52.5 |
|---|---|---|---|
| 1168040 | 4/1964 | Fed. Rep. of Germany | 81/59.1 |
| 2538741 | 12/1982 | France | 81/467 |
| 735393 | 3/1978 | U.S.S.R. | 81/467 |
| 856782 | 3/1979 | U.S.S.R. | 81/478 |
| 2148767 | 6/1985 | United Kingdom | 81/467 |

OTHER PUBLICATIONS

"CUSA TM Instruction Sheet," P/N 243 705 000 284, available from Cooper LaserSonics, Inc.

Primary Examiner—Edward M. Coven
Assistant Examiner—Randy Citrin
Attorney, Agent, or Firm—Vorys, Sater, Seymour & Pease

[57] ABSTRACT

An apparatus and method for assembly and disassembly of interchangeable surgical acoustic members includes a fixture for securing by a key a handpiece to which a tip and/or extender is attached. A torquing wrench has a tightening head and an untightening head on the same body, wherein the tightening head permits torquing of the tip and/or extender to a predetermined tightening torque in cooperation with a socket having a central bore therethrough so that the wrench and socket may be slid over an axially elongated combination and used at a point intermediate along the length thereof. In use, the handpiece is secured in the handpiece fixture and receives the tip and/or extender in a handtightened condition to be torqued to a predetermined limit by the torquing wrench while secured against rotation in the handpiece fixture. A table support structure for supporting a handpiece fixture for an alternative operation is also disclosed. The components are designed for a ready exchange of acoustic tips prior to, during, or after surgery in the sterile field with minimum inconvenience.

61 Claims, 5 Drawing Sheets

APPARATUS AND METHOD FOR ASSEMBLY AND DISASSEMBLY OF INTERCHANGEABLE SURGICAL ACOUSTIC MEMBERS

CROSS-REFERENCE TO RELATED APPLICATIONS

This application is a continuation of copending application, Ser. No. 782,306, filed Oct. 1, 1985, now abandoned, which is continuation-in-part of copending application, Ser. No. 761,495, filed Aug. 1, 1985, now abandoned.

BACKGROUND OF THE INVENTION

This invention relates to an apparatus and method for an assembly and a disassembly of interchangeable surgical acoustic members. More particularly, this invention relates to a fixture for securing a surgical handpiece for cooperating with a torquing wrench having a tightening head with predetermined torquing limits and a loosening head mounted on the same body. Still more particularly, this invention relates to a method of assembling and disassembling such interchangeable surgical acoustical members.

Ultrasonic surgical devices are known for performing a number of surgical procedures. A representative device is shown in U.S. Pat. No. 3,589,363 describing a hand-held instrument having an operative tip vibrating at a frequency in the ultrasonic range, and in which a handpiece includes a transducer. Connections are provided on the handpiece to a source of treatment fluid and a pump to withdraw suspended tissue particles in a fluid from an operative site. The tip is elongated and provided with a thickened shank portion formed with a pair of flats, originally intended to accommodate a wrench for tightening.

In practice, the design of such ultrasonic surgical devices depends not only on the technical and functional requirements of a resonant body, but also upon its surgical application. Thus, the length of the tip and its diameter to be acceptable for a useful surgical device in various operative site areas has developed over the years, based upon experience with such devices. In particular, it has been determined in the art that an especially useful arrangement incorporating proportioned surgical acoustic members, both from the standpoint of its surgical application and with respect to its manufacturability and costs, is based upon a combination of parts that are threaded together for easy interchange. The joint between the tip and the device is generally made at a point between a half-wave and quarter-wave length of the acoustic member in question.

However, as the length of the interchangeable part approaches a quarter wavelength, the stress at the threaded joint increases, thus requiring a greater force to maintain the coupling surfaces in appropriate contact during ultrasonic vibrations. In practice, it is important for intimate contact to be maintained between the coupling surfaces to maximize energy transfer, minimize mechanical losses, obtain consistent performance during surgical use of the device, and to minimize parasitic vibrations during operation. In particular, the latter may cause premature failure of either or both of the coupled acoustic members.

Experience with such devices has also determined an appropriate coupling force or torque for such systems. The coupling torque is sufficiently great that the acoustic members cannot be adequately fastened with normal finger force, requiring a wrench with an appropriate mechanical advantage. Thus, a technique for fastening and unfastening such surgical tips to such devices has been available to the art, as will be described in greater detail.

The techniques of fastening and unfastening the surgical tip to the device are based upon a number of constraints in the art. On the one hand, the design and size of the threaded joint between the tip and the acoustical member is made as small as possible to minimize the weight for the surgeon and to minimize visual interference with the surgical procedure. Partly because of such size, overtightening of the threaded joint is not desirable since overtightening may overstress the threaded joint resulting in its fracture. On the contrary, insufficient tightening can result in incomplete acoustical coupling, heating of the threaded joint, degraded surgical performance, and a potential for eventual catastrophic failure of the acoustic parts.

A system available to the art, which will be described in connection with FIGS. 1 and 2, has provided two torque wrenches, a tip socket, a stack socket and a holding fixture to provide operating room personnel with an ability to secure the handpiece of the surgical device, tighten the tip to the handpiece to a preset level, and then later untighten the interchangeable acoustic members used for each surgical case. Such an apparatus used a conventional tightening wrench, but some difficulty was experienced in providing enough force to loosen the ultrasonic tip after a surgical usage. Accordingly, a second wrench, for untightening, was provided as an adapted commercial device allowing disassembly of the acoustic members without allowing uncontrolled tightening by the use of a single direction clutch. Such an apparatus was intended for use in a non-sterile field and somewhat cumbersome as surgical devices developed to include curved and straight extenders. The availability of alternative tip structures for use by the surgeon resulted in a more elaborate and more complex device which is difficult and confusing to utilize, was not easily portable, and tended to be expensive to manufacture. In addition, such device was not readily sterilizable for use in an operative field for the convenience of changing tips during surgery.

Accordingly, it was a problem in the use of such a device to develop a simplified torque wrench to combine the tightening and loosening features in a single wrench, capable in this environment of cooperating with an existing handpiece holding fixture. One particular problem was that socket wrenches which were commercially available were not readily useable on elongated members because the available sockets are solid and not suited for use at a position intermediate an elongated member.

Accordingly, it is an overall object of this invention to provide a modified fixture for securing the handpiece of the surgical device for tightening and loosening a surgical tip secured to the handpiece.

It is another overall object of the invention to provide such a handpiece fixture which can be hand-held or readily mounted on a stand on a table to support the handpiece and handpiece fixture during assembly or disassembly.

It is still another object of the invention to provide such a handpiece fixture which is capable of accepting in a rotatably secure position various handpiece and tip combinations, such as are comprised by a standard straight handpiece or an angled handpiece, on the one hand, connected directly to straight, curved or flexible tips, or to straight or curved extenders to which the tip is attached.

It is still another object of the invention to provide such a fixture for a handpiece of the type described, wherein the relative rotation between the fixture, a handpiece, and the acoustic vibrator can be secured to a key as in the currently commercial embodiment so that the fixture and wrench according to this invention can be utilized with existing surgical devices and handpieces currently available to operating personnel.

It is another overall object of this invention to provide a convenient method and apparatus to facilitate a change in the fragmenting and related elements during a surgical procedure in a way which eliminates a need for removing the acoustic vibrator from the handpiece as in the prior art.

It is still another overall object of this invention to provide a torque wrench which is capable of sliding over an assembled and hand-tightened combination of a handpiece, tip, and/or extender and to provide a socket which is structurally accommodated to such an elongated subassembly.

It is still another object of this invention to provide a torque wrench with a socket assembly of the type described having both a tightening head preset to a predetermined torquing limit and a loosening head, arranged in such a way to preclude an operator from applying the wrench in an erroneous direction.

It is still another object of this invention to provide a fixture for use with such a wrench that can be used in hand to cooperate with the wrench in a scissor fashion, or be supported on a table support plate at the choice of the user.

It is a further overall object of this invention to provide such a handpiece torquing set in kit form for the convenience of medical personnel and arranged for easy sterilization within the sterile field so that the tips can be quickly and easily exchanged either prior to, during or after surgery with a minimum disassembly of the handpiece, while avoiding inadvertent damage to the exposed acoustic vibrator stack and human engineered to minimize operator error and confusion.

BRIEF SUMMARY OF THE INVENTION

Directed to achieving the foregoing objects of the invention and overcoming problems in connection with the tightening and loosening of an acoustic vibratory assembly having a transducer and a tip to a handpiece in a surgical device, the invention comprises a handpiece fixture for use in combination with a torquing wrench having a tightening head and a loosening head disposed in a common body for receiving a socket therein for engaging mating tool pads on a surgical tip to tighten the tip to form an acoustic vibrator tightened to a predetermined tightening tolerance.

The fixture includes a body, having a base surface and a thickness capable of being held in the hand of a user. A top surface includes an inclined portion merging into a top end surface defining an elongated keyway for receiving a key therein to secure a hand tightened preassembly of a handpiece acoustic vibrator in an elongated transverse opening passing through the body from the opposed side surfaces of the fixture. The opening is significantly defined in cross section by a circle having its radius at the center of an opening, portions of which merge with the segments of a circle having a second radius centered on an axis horizontally remote from the main axis of the opening and a second circle centered on an axis oblique to the main axis. Thus, the opening is defined by four connected arcuate surfaces to accommodate and secure various types of handpieces (straight or angled) in combination with various tips (straight or angled) in combination, when used, with various extenders (straight or angled). Preferably, the body is made of a suitable rigid plastic material and the transverse opening is defined in a block made from metal or other material of sufficient mechanical strength, and secured in an upper foremost location of the body by threaded fasteners. The lower surface of the fixture defines a plurality of openings for mating with extending pins on the upper surface of a table support device. The table support device includes a base plate which comprises a rectangular body to which are secured a plurality of table-engaging foot pads. Mediately disposed on the upper surface of the body is an upwardly-extending elongated support plate from which the fixture engaging pins extend, and further defining a transverse channel in the upper surface thereof.

The handpiece fixture is thus held by hand or mounted to a table support device positioned on a table to support the handpiece and the fixture during assembly or disassembly. When used by hand, the torquing wrench is positioned so that the handpiece fixture and wrench are used in a scissor-like fashion. When the operator uses the table support device, the wrench is positioned so that it may be pushed downwardly while holding the handpiece fixture against the table with the opposite hand of the operator. The transverse channel in the upwardly extending elongated support plate of the table support device is used during the disassembly of the tip from the extender.

The method of using the fixture and the wrench according to the invention includes the step of providing a handpiece fixture of the type described, hand-tightening a selected tip and/or extender to a transducer, selecting a socket having a bore therethrough for mating with the tip or extender, placing the socket on the tip or extender, sliding the torque wrench over the socket to engage the socket, rotating the wrench in a first tightening direction about the socket to tighten the tip or extender to a set predetermined torque. It is a feature of the socket and wrench that they may be axially slid over the axially elongated hand tightened subassembly of the transducer tip and/or extender.

In an alternative method of use, the handpiece fixture is positioned on the table support device so that the openings in the base portion thereof engage the pins extending from the table support plate, and the hand-tightened subassembly is secured by a key in the transversely extending opening in the handpiece fixture. A socket is slid over the subassembly, the wrench engages the socket, and the tip and/or extender is tightened with the torquing wrench.

After use, or to change a tip and/or extender, the untightening head of the torque wrench is used in conjunction with the handpiece fixture and/or the transverse slot in the table support device.

As described, the apparatus and method provides the user with a significantly simplified and enhanced capability to quickly and easily exchange a variety of tips either prior to, during, or after surgery, while requiring a minimum disassembly of the handpiece to facilitate quick attachment and removal.

BRIEF DESCRIPTION OF THE DRAWINGS

In the drawings:

FIG. 1 provides a basis for understanding a prior art method and apparatus for interchanging surgical acoustic members, wherein:

FIGS. 1(k) and 1(l) show the completion of the assembly by connecting the manifold assembly;

FIG. 5 shows a tip socket wherein

FIG. 6 illustrates an extender socket where

FIG. 9 is a view of the table support device wherein

The drawings are illustrative of the concept of the wrench to teach the selected art and should not unduly limit the invention which obviously could include other embodiments obvious to a person of ordinary skill in the art within the spirit of the invention.

DETAILED DESCRIPTION OF THE PREFERRED EMBODIMENT

In order to facilitate an understanding of the features and advantages of the fixture and wrench according to the invention and the method of assembly and disassembly which are features of the foregoing invention, a description is provided of the prior art method of assembly and disassembly as applied to an apparatus of the type described in U.S. Pat. No. 3,589,363, for example, the disclosure of which is incorporated by reference.

Figure 1:
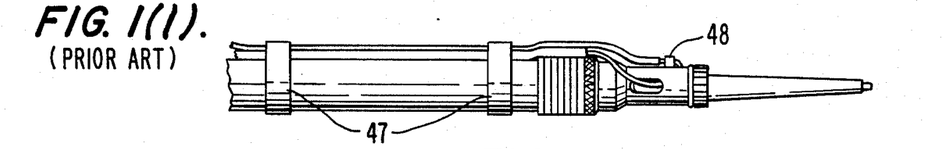
Figure 1A:
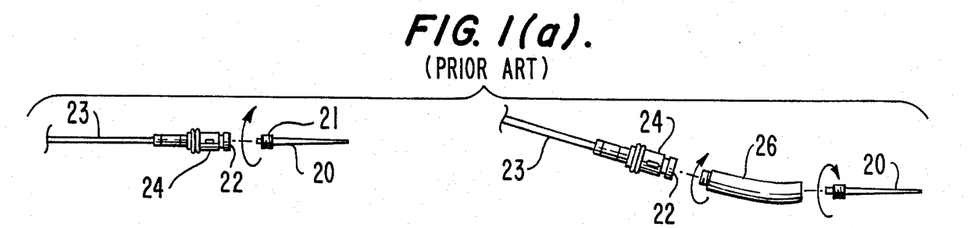
FIG. 1(a) depicts the attachment of a tip to a transducer, with or without an extender.
Figure 1B:
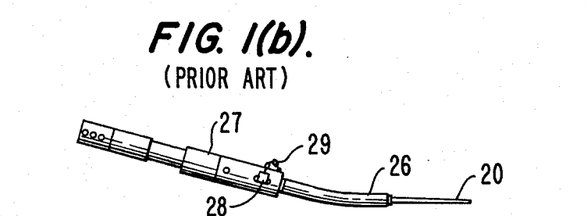
FIG. 1(b) shows the use of a stack socket to prepare the subassembly for tightening.
Figure 1C:
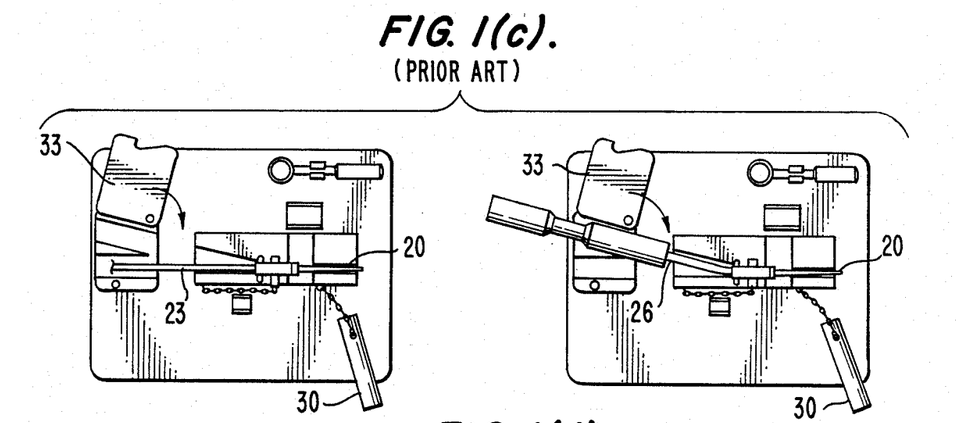
FIG. 1(c) shows the manner of securing the stack socket-tip-transducer subassembly for tightening.

In FIG. 1, and more particularly in FIGS. 1(a)-1(h), a prior art method of assembly of a surgical device, showing the steps of assembling an acoustic vibrator, a nose cone assembly for the acoustic vibrator, a flue assembly, a handpiece, and a manifold, is described for both an assembly which includes only a tip, or with a curved or straight extender interposed between the tip and a transducer. Thus, as shown in FIG. 1(a), a tip 20 having a flange 21 with tool pads is hand tightened by threading into a mating opening 22 of a transducer 23. The transducer has an elongated slot 24 for receiving a key. At the righthand portion of FIG. 1(a), a similar assembly is shown in which an extender 26 is interposed between the tip 20 and the transducer 23. In either case, the subassembly is hand tightened to form an acoustic vibrator. As shown in FIG. 1(b), when an extender 26 is used, the acoustic vibrator is placed in a stack socket 27 having a keyway 28 and secured by a key-chain 29 in a slot in the body of stack socket to mate with the opening 24 in the transducer after alignment. As seen in FIG. 1(c), a tip socket 30 is provided as part of a set, shown diagrammatically in FIG. 2. As provided, the set includes the stack socket 27, the tip socket 30, an assembly wrench 31, a disassembly wrench 32, and a hold down plate 33 which is pivotable about pin 34 to secure the subassembly in openings or grooves in the torquing set. As seen in FIG. 1(c), when only a tip is used, the acoustic vibrator assembly is axially aligned, whereas if a curved extender is used, the relationship between the grooves beneath the hold down plate 33 and associated grooves in the set is such to accommodate the angle subtended by the extender-transducer subassembly. In either event, the hold down plate 33 is rotated to an open position and the acoustic vibrator is positioned in the torquing kit in an appropriate groove. When only a tip is used, a single key will mate with the opening 24 in the transducer, whereas if an extender is used, a pair of keys is used in vertically spaced slots to secure the acoustic vibrator therein.

Figure 1D:
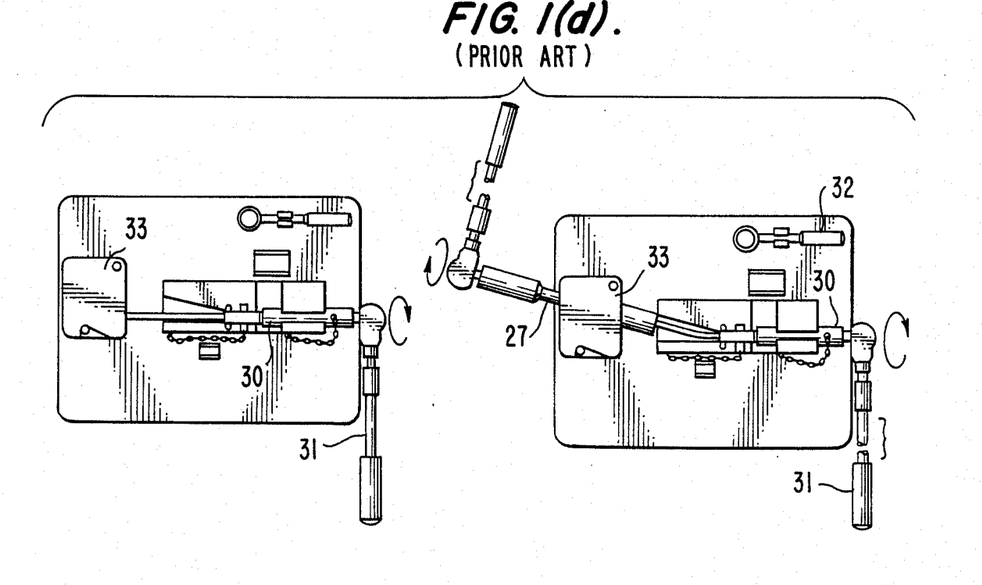
FIG. 1(d) shows the tightening operation with the use of a tip socket.
Figure 2:
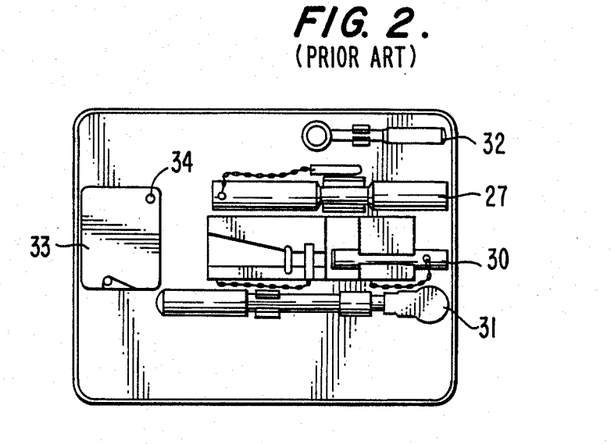
FIG. 2 is a depiction of a prior art kit containing both an assembly wrench and disassembly wrench with a stack socket and a tip socket for performing the operations of FIG. 1.

As shown in FIG. 1(d), the hold down plate 33 is pivoted to its closed position, and the tip socket 30 is slid over the tip 20. An assembly wrench 31 is attached to the tip socket and rotated until a predetermined, preset torque is achieved according to the construction of the assembly wrench, and the wrench 31 is removed. The tightening wrench 31 is then attached to the stack socket 30 and rotated until a predetermined torque is achieved so that both the extender and the tip have been tightened to the predetermined torque.

Figure 1E:
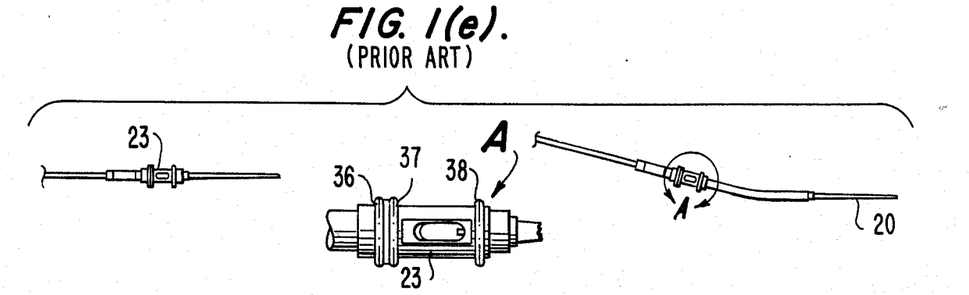
FIGS. 1(e) and 1(f) show the attachment of the nose cone assembly.
Figure 1F:
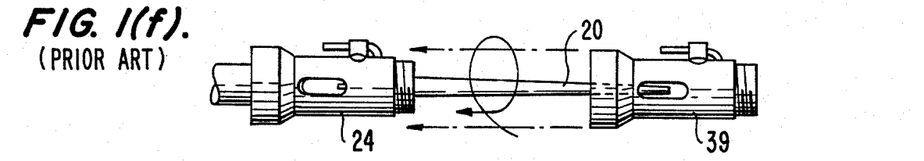

After the acoustic vibrator is assembled as shown in FIGS. 1(a)-1(d), a nose cone is assembled as shown in FIGS. 1(e) and 1(f). A pair of O-rings 36 and 37 is provided adjacent a flange on the transducer remote from the tip 20 and seated therein. A third O-ring 38 is provided in a groove on the transducer 23 proximate to the tip 20 and a nose cone 39 is axially slid and rotated to seat the nose cone 39 to the acoustic vibrator by threaded engagement.

Figure 1G:
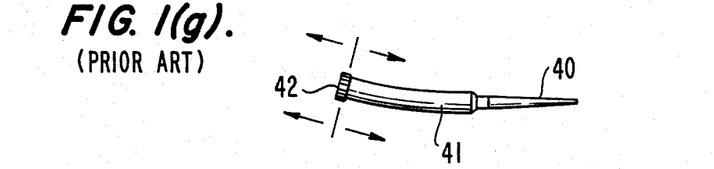
FIGS. 1(g) and 1(h) show the attachment of the flue assembly.
Figure 1H:
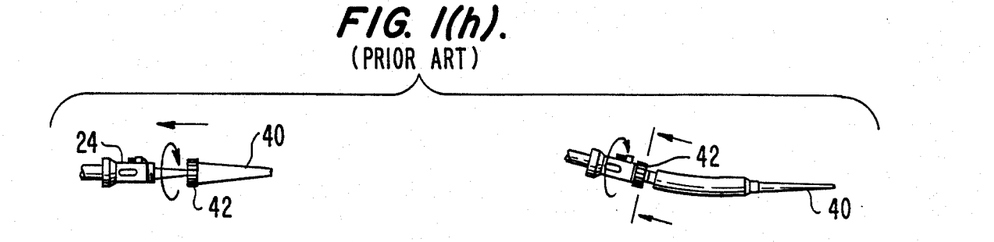

Thereafter, as shown in FIGS. 1(g) and 1(h), a flue 40 secured to a body 41 having a nose cone adapter 42 at one end thereof is slid over the tip-extender combination. Where only the tip 20 is used, only the flue 40 and nose cone adapter 42 are needed. The flue 40 is then aligned relative to the tip 20 to centralize the tip 20 within the flue 40.

Figure 1I:
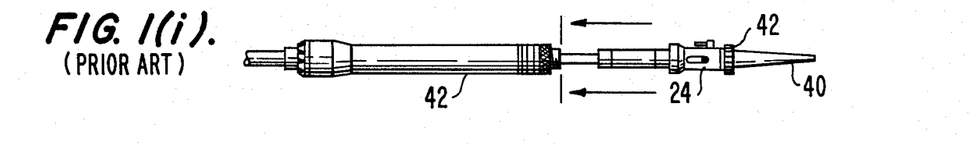
FIGS. 1(i) and 1(j) show the attachment of the handpiece assembly to the acoustic vibrator and nose cone with the flue.
Figure 1J:
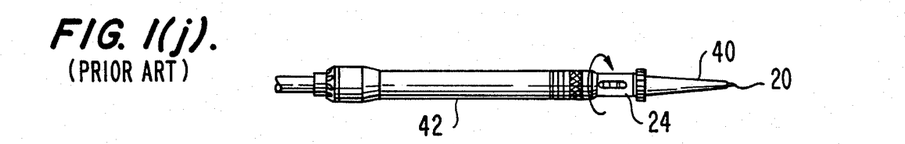
Figure 1K:
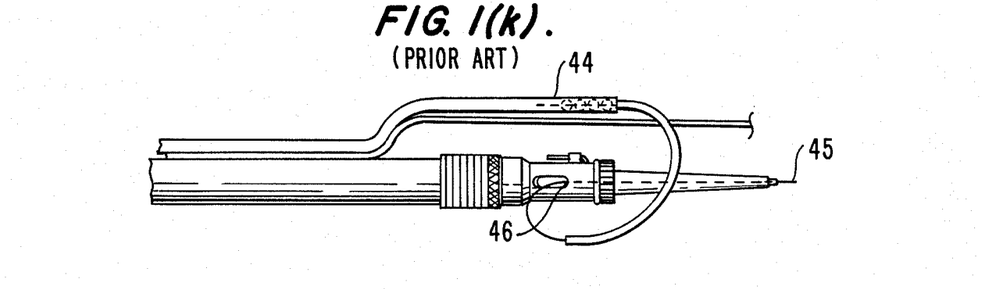

Thereafter, the subassembly comprising the acoustic vibrator, the nose cone, and the flue is inserted into a handpiece housing 42 and rotated until snug, as shown in FIGS. 1(i) and 1(j). Thereafter, an aspiration tube 44 with a flexible applicator cable 45 is inserted through a slot in the nose cone 38 and fed through an aspiration port 46 within the nose cone. By pulling the cable 45 through the tip 20, the aspiration tube 44 will attach to the aspiration port 46. As shown in FIG. 1(l), the irrigation tube is secured to an irrigation port 48, and clips 47 secure the tubing to the body of the instrument. The irrigation and aspiration tubing is then connected to the instrument.

To disassemble the acoustic vibrator after surgical procedure, the above-described assembly instructions are reversed, using a disassembly wrench 32.

Figure 3:
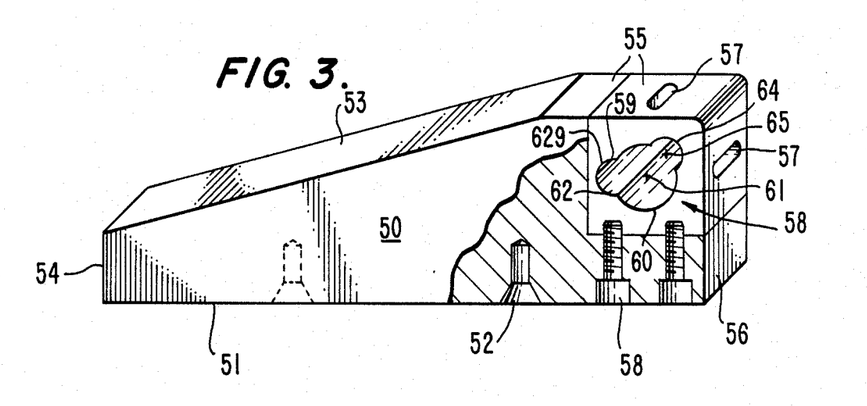
FIG. 3 is a perspective view, partly in section, of the handpiece fixture according to the invention.

An improved fixture according for use to the invention is shown in FIG. 3 for securing the assembled handpiece acoustic members therein to complete tightening. The fixture includes a body 50 defining a lower surface 51 having a pair of openings 52 therein. The body 50 defines a sloped upper surface 53 merging into a left end surface 54 and a generally horizontal upper surface 55 merging into a right end surface 56 having a height greater than the height of the surface 54. Such a structure, which resembles a staple gun, is designed to be held conveniently in the hand of the user. The upper surface 55 defines a key slot 57 merging into a transversely extending opening 58 for receiving and securing the handpiece. The structure of the transverse opening 58 is designed to receive a straight handpiece, an angled handpiece, which is angled at any angle up to ninety degrees, a straight extender, a curved extender, or other handpiece assemblies. Thus, the opening 58 is defined by a pair of arcs 59 and 60 about a center 61, a third arc 62a defined about a center 62 located horizontally remote from the center axis 61 and an arc 64 located about a center 65 at an upwardly oblique angle from the center axis 61. The handpiece which is axially elongated and its tip (or tip/extender combination) are fixedly secured by a key inserted into the key slot 57 to couple the fixture with the handpiece to prevent relative rotation between the fixture, handpiece and acoustic vibrator. The fixture according to FIG. 3, in conjunction with the torque wrench of FIG. 4, significantly enhances the ability of operating room personnel to change fragmenting and related elements during the operating procedure, thus eliminating the necessity of removing the acoustic vibrator from the handpiece proper as had been required in connection with the procedure described in connection with prior art FIG. 1. The new fixture is intended to accept the assembled handpiece.

FIG. 4 is a diagrammatical illustration of the torque wrench 70 constructed for use with the invention. The wrench 70 comprises a housing or body 71 connected to a handle 72. The body defines a first socket receiving opening 73 for tightening to a predetermined torque and an adjacent socket receiving opening 74 for loosening a tip or extender from the transducer. Preferably, the tightening head of the wrench only tightens when the wrench is rotated in a clockwise direction and incorporates a one-way clutch to prevent a reverse (or loosening) operation. Conversely, the loosening head of the wrench preferably only loosens when rotated in a counterclockwise direction and likewise incorporates a one way clutch operated in reverse to that associated with the tightening action in order to prevent tightening and to minimize a possibility of human error. The tightening head 73 includes a sleeve insert receiver 76, a bearing plate 77 for retaining a clutch bearing 78, and a retaining ring 79 to form an operative assembly, as is well known in the art. The clutch bearing 78 is pressed into a cam member 80 and the bearing plate 77 is positioned in the body 71. The cam assembly is inserted into the body to mesh with the bearing plate 77 and the handle 72 is added as a subassembly.

The handle 72 includes a lubricated member 82, (either a ball or roller) a ball or slider 83, biased by a spring 84, and a spring retaining member 85 to provide a preselected amount of torquing according to positioning of the screw 86. Labels 87 and 87a bearing suitable indicia are respectively secured on the tightening and loosening heads 73 and 74 to indicate the direction of operation of the wrench.

The loosening head 74 includes a sleeve insert member 88, a roller clutch 90, and a bearing plate 92 to define the socket receiving opening for tightening. It is a feature of this torquing wrench to be able to mate with a socket which is axially slidable along the elongated member, such as the transducer, tip, and extender, if used.

While the individual elements of the wrench are known, for the first time they are being used together in a novel combination for applications in a surgical environment. The surgical and especially the sterile surgical field present a set of unique technical requirements in that:

(a) the device must be reasonably light and easy to use by a non-technical person, such as a nurse;

(b) the wrench must be reasonably inexpensive so that, as an accessory, its cost benefit ratio will be considered advantageous to the customer and the producer; and (c) the wrench must remain in calibration for long periods of time or the proper function of the ultrasonic surgical device it services will be impaired. Hospital personnel traditionally have no way of checking the calibration of the device.

Figure 4A:
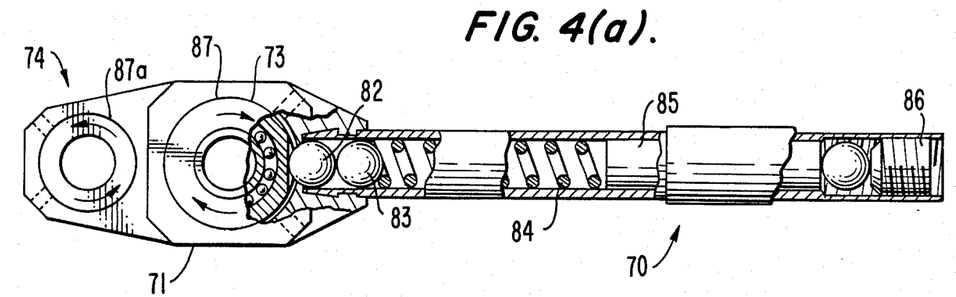
FIGS. 4(a) and 4(b) together show a top view and side view, partially in section, of a torquing wrench according to the invention.
Figure 4B:
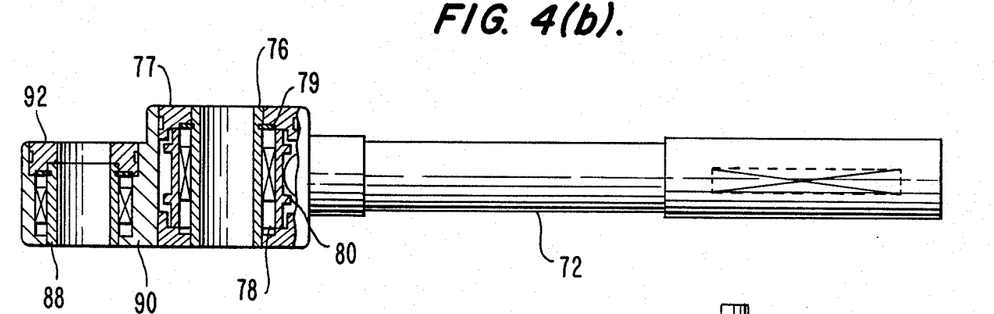

As shown in FIGS. 4(a) and 4(b), the design of the torque wrench addresses requirement (a) in a number of ways to provide a number of advantages.

First, the shape of the head is stepped and is thus human engineered to require its application in the proper direction only.

Second, the sleeves which accept the hex sockets are stepped to prevent an improper insertion of the sockets.

Third, the head material is aluminum for light weight.

Fourth, the handle length is proportioned for proper balance and yet easy mechanical advantage.

The design of the torque wrench in FIGS. 4(a) and 4(b) also addresses the cost requirement.

An application of one way roller (clutch) bearings to a torque wrench is a low cost, functionally effective application of a well known art to a new field. One way ratchet devices which are usually seen in this type of device are complex, expensive or unreliable. The one way roller clutch is a simple, elegant solution to an old problem and is especially suitable to the surgical environment in question.

The design of the torque wrench in FIGS. 4(a) and 4(b) addresses the requirement of calibration as follows:

The two element mechanism in the handle: comprising elements 82 and 83 of FIG. 4(a), provides a way to apply the spring force in an appropriately constrained fashion so that the torque applied is consistent and repeatable without recalibration for long periods of time. Normal torque wrenches lose their calibration after hundreds of cycles. This device is designed to operate for thousands of cycles without recalibration.

Thus, the wrench of FIGS. 4(a) and 4(b) provides for an unlimited angular rotation of the torquing device without fear of overtightening. Moreover, it provides a device with a resettable torque which allows a tightening of unlimited length members. These features are in constrast to devices which do not feature open or through sockets, ratchet wrenches which have a limited rotation, or open end torque limiting wrenches in which, if the present angular rotation were exceeded, the torque limitation would no longer be available.

Figure 5A:
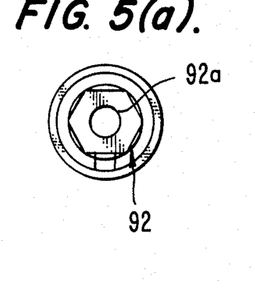
FIG. 5(a) is an end view.
Figure 5B:
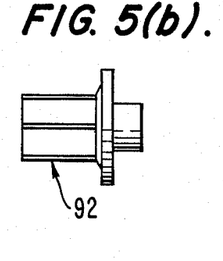
FIG. 5(b) is a side view thereof.
Figure 6A:
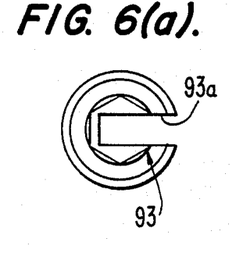
FIG. 6(a) is an end view and FIG. 6(b) is a side view of the extender socket.
Figure 6B:
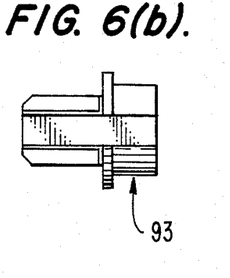

FIGS. 5 and 6 respectively show a tip socket 92 and an extender socket 93 to be received in the tightening and loosening socket receiving opening as described. Preferably, the sockets define a bore 92a, 93a therethrough so that the sockets may also be slid axially along any elongated member, such as the tip and extender of this invention. Preferably, the bore 93a in the extender socket is laterally extended to define a slot as shown in FIG. 6 so that the curved surface of a curved extender can be readily accommodated. The mating portion of the socket is for the wrench preferably hexagonal. In use, the handpiece is secured to the handpiece fixture as discussed above and the tip and/or extender is screwed thereto in a finger tight fashion. An appropriate socket, such as a tip socket 92 for a tip 20 or an extender socket 93 for an extender 26, is selected and axially slid over the tip 20 or transversely placed over the extender 26 respectively to engage the tool pads on the tip or extender. The torque wrench 70 is then slid over the elongated tip/extender structure and engages the selected socket.

Figures 7, 8:
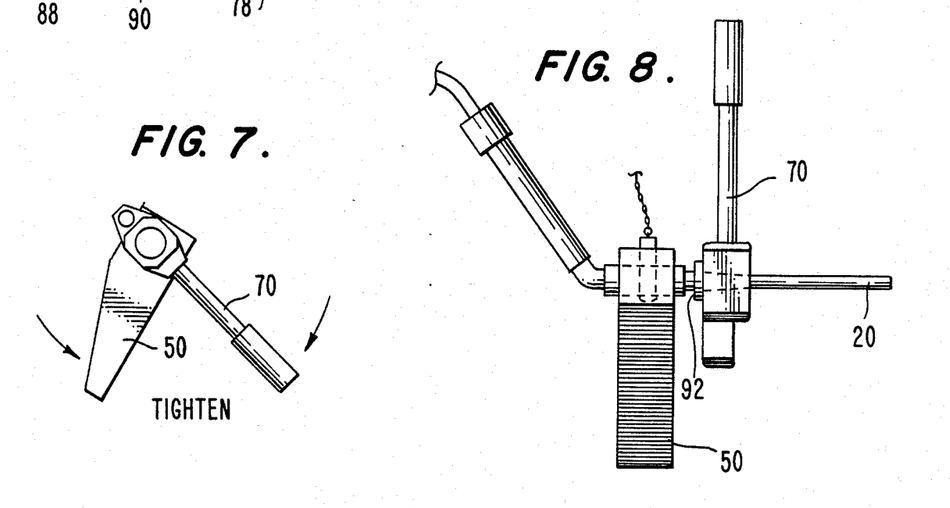
FIG. 7 is a diagrammatic view of the cooperation of the fixture and torquing wrench acting as a scissor, when the operator prefers to hand hold the fixture.
FIG. 8 is a top diagrammatic view of a handpiece assembly secured in the handpiece fixture with the torque wrench engaging an exchangeable socket for exchanging the tip or other acoustical member.

FIG. 7 shows the use of the fixture 50 and the wrench 70 to perform the operation as discussed above when the operator holds the fixture 50 in hand. Thus, the cooperation between the fixture and the wrench acts as a scissor to perform the assembly or disassembly operation as described.

FIG. 8 shows a view in diagrammatic fashion of an angled handpiece secured by a key assembly to the handpiece fixture 50 wherein the tip or other acoustic member is engaged by an exchangeable socket 92 for rotation by the torque wrench 70, in summary of the discussion above.

Figure 9A:
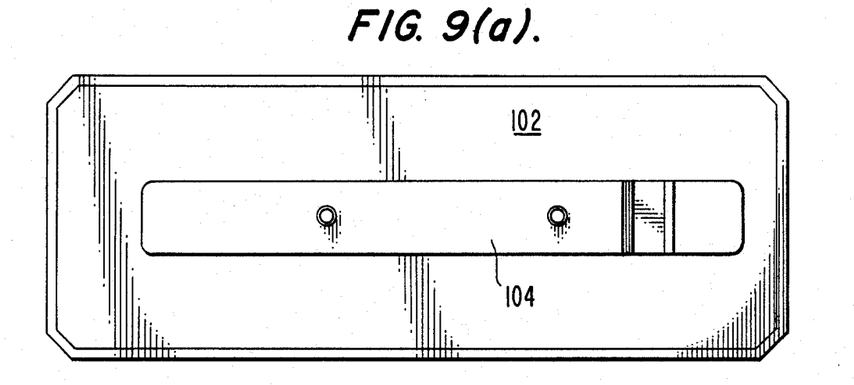
FIG. 9(a) is a top view thereof and FIG. 9(b) is a side elevational view thereof partially in section.
Figure 9B:
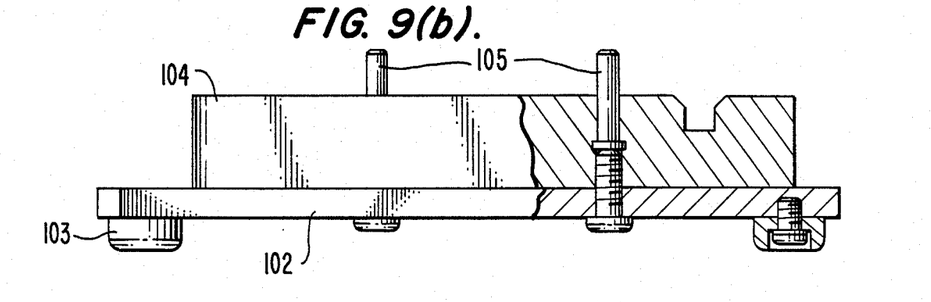

FIGS. 9a and 9b show a table support device for mounting the fixture of FIG. 3 thereon when an operator wishes to utilize the method and apparatus according to this invention in connection with the table. The table support comprises a base plate 102 having a plurality of table-engaging foot-pads 103 to which is secured an upwardly-extending rectangular member 104 having a plurality of upwardly extending pins 105 from the upper surface thereof. The pins 105 engage the mating recesses 52 in the lower surface 51 of the fixture shown in FIG. 3.

Figure 10:
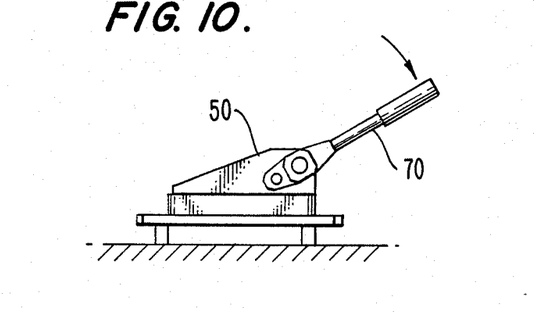
FIG. 10 is a side elevational view of the table support member of FIG. 9, securing the fixture of FIG. 3, for use with the wrench of FIG. 4.

FIG. 10 is a diagrammatic illustration of the support member of FIG. 9 and the fixture of FIG. 3 during use. The wrench is positioned so it is pushed down while the operator holds the fixture against the table with the other hand.

A significant advantage of the invention is that all parts of the handpiece torquing set are capable of sterilization, such as by ethylene oxide gas, so that the tips and other parts may be interchanged during surgery in the sterile field. As in the case of the prior art embodiment, the components of the system are preferably provided in the form of a set which includes a handpiece fixture, a table support plate, a torquing wrench, a plurality of sockets, a key, and instructions in a convenient pack.

Figure 11A:
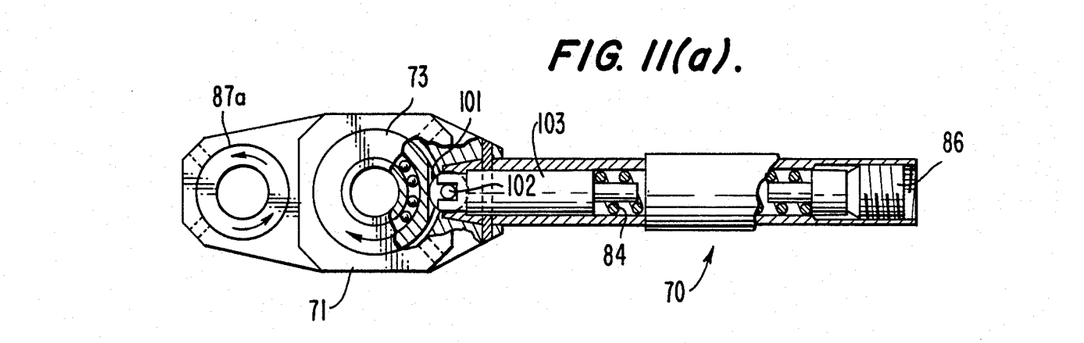
FIGS. 11(a) and 11(b) together show a top view and side view, partially in section, of an alternative embodiment of the torquing wrench of FIGS. 4(a) and 4(b).
Figure 11B:
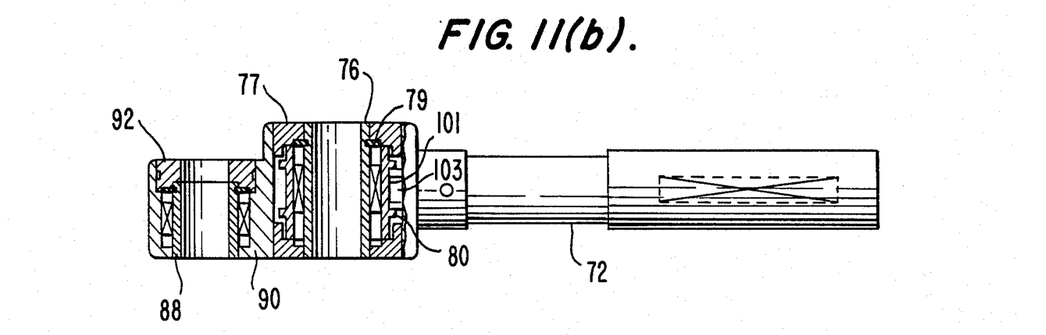

FIGS. 11(a) and 11(b) show an alternative embodiment of the torquing wrench which is quite similar to the embodiment of FIGS. 4(a) and 4(b). In this alternative embodiment, the ball members 82 and 83 are replaced by a roller member 101 having its outermost surface in line contact with the cam member 80. The roller member 101 is restrained against rotational movement by a pin 102 slidably located in a pair of openings in an elongated tappet member 103. Thus, the roller member is free to slide to the left and right as shown in FIG. 11(a). The roller member 101 is in line contact with the cam, rather than in point contact, as in the case of the ball 82 in FIG. 4(a). As in FIG. 4(a), the tappet member 102 is biased by a spring 84. The advantages and operational features of the wrench embodiment in FIG. 11(a) are thus the same as in the embodiment of FIG. 4(a).

This invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. A method for assembling interchangeable acoustic members to a surgical handpiece, said method comprising the steps of providing a handpiece fixture having a body defining a handpiece receiving opening therethrough for rotatably securing said handpiece against rotation during torquing; hand tightening a selected acoustic member to a transducer on said handpiece; selecting a socket having a bore therethrough for mating with said acoustic member; placing said selected socket on said acoustical member by sliding said socket over and along a length of said acoustic member through said bore; sliding a torque wrench over and along a length of said acoustic member to engage said socket; rotating said wrench in a first tightening direction about said socket to tighten the acoustic member to a predetermined torque; and removing said wrench and said socket from said acoustic member.

2. The method as set forth in claim 1, wherein the step of tightening by rotating said wrench is accomplished while holding said fixture in the hand of a user.

3. The method as set forth in claim 1, wherein the step of tightening is accomplished further including the step of supporting said handpiece fixture on a table support device.

4. A method for assembling and/or disassembling an acoustic member to a surgical handpiece, said method comprising:
   securing the handpiece against rotation during torquing in a handpiece-receiving opening of a handpiece fixture,
   hand tightening the acoustic member to the handpiece,
   placing a socket, which has a bore therethrough which mates with the acoustic member, on the acoustic member by sliding the socket through the bore thereof along a length of the acoustic member, sliding a torque wrench over and along a length of the acoustic member to engage the socket, and rotating the wrench in a tightening direction about the socket to tighten the acoustic member to a predetermined torque.

5. The method of claim 4 including, thereafter, removing the wrench and the socket from the acoustic member.

6. The method of claim 4 including,
before said hand tightening step, selecting the acoustic member from among a plurality of interchangeable acoustic members for the handpiece.

7. The method of claim 4 including,
said rotating step including the user holding the fixture in his hand while rotating the wrench.

8. The method of claim 4 including,
said rotating step including the handpiece fixture being supported on a table support.

9. The method of claim 4 including,
after said removing step, placing a socket having a bore therethrough which mates with the acoustic member on the acoustic member, sliding a torque wrench over the socket to engage the socket in a loosening opening of the wrench, and rotating the wrench in a loosening direction about the socket to loosen the acoustic member.

10. The method of claim 9 including,
said loosening direction being opposite to said tightening direction.

11. The method of claim 9 including,
said loosening opening being in the same torque wrench as said tightening opening and spaced therefrom.

12. The method of claim 4 including,
said hand tightening step including hand tightening the acoustic member to a transducer on the handpiece.

13. An apparatus for assembling and/or disassembling an acoustic member, said apparatus comprising:
a surgical handpiece,
a fixture comprising a body member, said body member including a defining means for defining a handpiece-receiving opening extending transversely therethrough for receiving said surgical handpiece therein, said body member including a securing means for securing said surgical handpiece in position in said handpiece-receiving opening, and
a torquing wrench means, including a first socket having a first socket bore therethrough and which is open at both ends, which is retained in scissor-like cooperating relationship with said fixture for torquing an acoustic member to a predetermined torque value into place on said surgical handpiece, after passing an end of the acoustic member through said first socket bore, and while said securing means secures said surgical handpiece against rotation in and relative to said body member.

14. The apparatus of claim 13 including,
said body member including a body member outer surface, and
said body member defining a key slot communicating said body member outer surface with said handpiece-receiving opening.

15. The system of claim 14 including,
said key slot forming at least a portion of said securing means.

16. The apparatus of claim 13 including,
said body member having a first end and a second end, and
said body member including at said first end a first body portion through which said handpiece-receiving opening passes, and an elongated second body portion attached to said first body portion and tapering so as to be thinner at said second end than at the second body portion adjacent to said first body portion.

17. The apparatus of claim 13 including,
said handpiece-receiving opening having its periphery defined by first, second, third and fourth arcs, said first and second arcs being defined by a first center, said third arc being defined by a second center spaced from said first center and said fourth arc being defined by a third center spaced from said first and second centers.

18. The apparatus of claim 17 including,
said second center being spaced horizontally from said first center, and
said third center being at an upwardly-oblique angle from said first center.

19. The apparatus of claim 13 including a support device comprising a base plate; and a holding means for holding said fixture relative to said base plate.

20. The apparatus of claim 19 including,
said fixture having a lower surface and defining a pin opening in said lower surface, and
said holding means comprising a pin means for passing through said base plate and engaging in said pin opening.

21. The apparatus of claim 19 including,
said support device comprising an upwardly-extending structure secured to said base plate for receiving said fixture thereon.

22. The apparatus of claim 13 in which said torquing wrench means includes a handle and a body connected to said handle, and
said body defines a first socket receiving opening means for receiving said first socket therein and for engaging the acoustic member and tightening the acoustic member on said handpiece, and a second socket receiving opening which is open at both ends thereof.

23. The apparatus of claim 22 including,
said torquing wrench means including a one-way roller clutch bearing adjacent to said first socket receiving opening, and a biasing means for biasing said clutch bearing to said predetermined torque value, and
said biasing means including a roller contact means contacting said clutch bearing, a spring means disposed in said handle for biasing said roller contact means, and an adjusting means for adjusting the compression of said spring means to determine said predetermined torque value.

24. The apparatus of claim 23 including,
said roller contact means comprising a roller ball member.

25. The apparatus of claim 23 including,
said roller contact means comprising a roller member.

26. The apparatus of claim 25 including,
said spring means comprising a spring having a longitudinal spring axis,
said roller member having a longitudinal roller axis, and
said roller axis being perpendicular to said spring axis.

27. The apparatus of claim 22 including, said torquing wrench means including a second socket having a second socket bore therethrough and which is open at both ends, said body defining a second socket receiving opening for receiving said second socket therein, and said second socket receiving opening being open at both ends and spaced from said first socket receiving opening.

28. An apparatus for assembling and/or disassembling an elongated surgical acoustic member, said apparatus comprising:

a surgical handpiece, a fixture comprising a body member, said body member including a defining means for defining a handpiece-receiving opening extending transversely therethrough for receiving said surgical handpiece therein, said body member including a securing means for securing said surgical handpiece in position in said handpiece-receiving opening, a torquing wrench means, which includes a first socket having a first socket bore therethrough and which is open at both ends, for torquing an elongated surgical acoustic member to a predetermined torque value into place on said surgical handpiece, after an end of the acoustic member has passed through said first socket bore, and while said securing means is securing said surgical handpiece against rotation in and relative to said body member, and said first socket bore being structurally adapted to receive therethrough and be axially slidable relative to the elongated surgical acoustic member.

29. An apparatus for assembling and/or disassembling an acoustic member, said apparatus comprising:

a surgical handpiece having a mating slot.

a fixture comprising a body member, said body member including a defining means for defining a handpiece-receiving opening extending transversely therethrough for receiving therein said surgical handpiece, said body member including a securing means for securing said surgical handpiece in position in said handpiece-receiving opening, a torquing wrench means, which includes a first socket having a first socket bore therethrough and which is open at both ends, which is retained in scissor-like cooperating relationship with said fixture for torquing an acoustic member to a predetermined torque value into place on said surgical handpiece, after an end of the acoustic member has passed through said first socket bore, and while said securing means is securing said surgical handpiece against rotation in and relative to said body member, said body member including a body member outer surface, said body member defining a key slot communicating said body member outer surface with said handpiece-receiving opening, and said securing means including a key means for engaging through said key slot said mating slot of said handpiece for securing said handpiece and said body member against relative rotation.

30. A surgical system comprising:

a surgical handpiece, a fixture comprising a body member, said body member including a defining means for defining a handpiece-receiving opening extending transversely therethrough for receiving said surgical handpiece therein, said body member including a securing means for securing said surgical handpiece in position in said handpiece-receiving opening, an acoustic member, and a torquing wrench means, which includes a first socket having a first socket bore therethrough and which is open at both ends, for torquing said acoustic member to a predetermined torque value into place on said surgical handpiece, after an end of said acoustic member has passed through said first socket bore, and while said securing means is securing said surgical handpiece against rotation in and relative to said body member.

31. A torque wrench for assembling or disassembling an acoustic member to or from a surgical handpiece, said torque wrench comprising:

a head member, an elongated handle having a longitudinal axis, a distal end and a proximal end, and being secured at said distal end to said head member, a first socket having a first socket bore passing therethrough and which is open at both ends, said head member defining a first socket receiving opening, which is open at both ends, and in which said first socket is received, a clutch means including a one-way roller clutch bearing adjacent to said first socket receiving opening and a biasing means for biasing said clutch bearing to a predetermined torque, said biasing means including a roller contact means contacting said one-way roller clutch bearing, a spring means disposed in said handle for biasing said roller contact means, and an adjusting means for adjusting the compression of said spring means to determine said predetermined torque, said spring means extending along the longitudinal axis of said elongated handle, said adjusting means including an adjustment screw at said proximal end of said handle and operatively engageable with said spring means.

32. The wrench of claim 31 including, a second socket having a second socket bore passing therethrough and which is open at both ends, and said head member defining a second socket receiving opening spaced from said first socket receiving opening which is open at both ends for receiving said second socket therein.

33. The wrench of claim 32 including, said first socket receiving opening being axially longer than said second socket receiving opening.

34. The wrench of claim 31 including, said roller contact means comprising a roller ball member.

35. The wrench of claim 31 including, said roller contact member comprising a roller member.

36. The wrench of claim 35 including, said spring means comprising a spring having a longitudinal spring axis, said roller member having a longitudinal roller axis, and said roller axis being perpendicular to said spring axis.

37. The wrench of claim 31 including, said roller contact means comprising a first roller ball contacting said clutch bearing and a second roller ball contacting said first roller ball and said spring means.

38. The wrench of claim 31 including,
said handle having a handle longitudinal axis,
said head member having upper and lower surfaces which said first socket receiving opening engages at opposite ends thereof, and
said handle longitudinal axis passing between said upper and lower surfaces.

39. The wrench of claim 31 adapted to receive a curved extender having a curved profile and positionable in said first socket bore,
said first socket being an extender socket, and
said first socket bore being laterally extended to define a slot to accommodate therethrough said curved surface of said curved extender.

40. The wrench of claim 31 in which,
said one-way clutch bearing including means for preventing a loosening operation when said elongated handle is rotated in a counter-clockwise direction.

41. The wrench of claim 31 including,
said head member having a stepped shape.

42. The wrench of claim 31 including,
said one-way roller clutch bearing including a cam member, and said spring means pressing said roller contact means in contact with said cam member.

43. The wrench of claim 31 including,
said head member having a head member top and a head member side,
said handle being fixedly secured to said head member side, and
said first socket bore engaging said head member top.

44. An assembly comprising:
(1) a fixture which has a means for defining a handpiece-receiving opening therethrough for securing a surgical handpiece therein against rotation during a torquing procedure, and a bottom surface opening; and
(2) a support device associated with said fixture, said support device comprising:
a base plate,
an upwardly-extending structure secured to said base plate and having a configuration for receiving said fixture thereon in an at least partially holding manner,
a pin passing up through said base plate inside of said upwardly-extending structure and adapted to extend into said bottom surface opening of said fixture when said fixture is positioned in said upwardly-extending structure, and
at least one fixture support-engageable foot pad connected to and positioned beneath said base plate.

45. A fixture for securing a surgical handpiece against rotation during a torquing procedure, said fixture comprising:
a first body member defining a handpiece-receiving opening extending transversely therethrough and structurally adapted for receiving a surgical handpiece therein,
said first body member including a body member outer surface and a securing means for securing in said handpiece-receiving opening the surgical handpiece against rotation during a torquing procedure,
said securing means including said first body member defining a key slot communicating said body member outer surface with said handpiece-receiving opening, and
an elongated second body member attached to and tapering away from said first body member.

46. The fixture of claim 45 including,
a body member securing means for securing said second body member to said first body member.

47. The fixture of claim 46 including,
said body member securing means comprising at least one bolt.

48. The fixture of claim 46 including,
said body member securing means passing up through an opening in a lower surface of said first body member.

49. The fixture of claim 45 including,
said second body member having a notch in an upper corner thereof and said first body member fitting into said notch and being attached thereto.

50. The fixture of claim 45 including,
said first body member being formed of a first material, and
said second body member being formed of a second material different than said first material.

51. The fixture of claim 45 including,
said handpiece-receiving opening having its periphery defined by first, second, third and fourth arcs, said first and second arcs being defined by a first center, said third arc being defined by a second center spaced from said first center, and said fourth arc being defined by a third center spaced from said first and second centers.

52. The fixture of claim 51 including,
said second center being spaced horizontally from said first center, and
said third center being at an upwardly-oblique angle from said first center.

53. The fixture of claim 45 including,
said second body member defining a lower surface, a left end surface, and a sloped upper surface which merges into said left end surface,
said first body member defining a right end surface having a height greater than the height of said left end surface, and a horizontal upper surface merging into said right end surface, and
said surfaces being proportioned to be held conveniently in the hand of the user.

54. A fixture for securing a surgical handpiece having a mating slot against rotation during a torquing procedure, said fixture comprising:
a first body member defining a handpiece-receiving opening extending transversely therethrough and structurally adapted for receiving a surgical handpiece having a mating slot therein,
said first body member including a body member outer surface and a securing means for securing in said handpiece-receiving opening the surgical handpiece against rotation during a torquing procedure,
said securing means including said first body member defining a key slot communicating said body member outer surface with said handpiece-receiving opening,
a second body member attached to said first body member, and
said securing means including a key means for engaging through said key slot the mating slot of the handpiece for securing said first body member and the surgical handpiece against relative rotation.

55. A fixture for securing a surgical handpiece against rotation during a torquing procedure, said fixture comprising:
- a first body member defining a handpiece-receiving opening extending transversely therethrough and structurally adapted for receiving a surgical handpiece therein,
- said first body member including a body member outer surface and a securing means for securing in said handpiece-receiving opening the surgical handpiece against rotation during a torquing procedure,
- said securing means including said first body member defining a key slot communicating said body member outer surface with said handpiece-receiving opening,
- a second body member attached to said first body member and having a notch in an upper corner thereof, and
- said first body member fitting into said notch and being attached thereto.

56. A fixture for securing a surgical handpiece against rotation during a torquing procedure, said fixture comprising:
- a first body member defining a handpiece-receiving opening extending transversely therethrough and structurally adapted for receiving a surgical handpiece therein,
- said body member including a body member outer surface and a securing means for securing in said handpiece-receiving opening the surgical handpiece against rotation during a torquing procedure,
- said securing means including said body member defining a key slot communicating said body member outer surface with said handpiece-receiving opening,
- a second body member attached to said first body member, and
- said handpiece-receiving opening having its periphery defined by first, second, third and fourth arcs, said first and second arcs being defined by a first center, said third arc being defined by a second center spaced from said first center, and said fourth arc being defined by a third center spaced from said first and second centers.

57. The fixture of claim 56 including,
- said second center being spaced horizontally from said first center, and
- said third center being at an upwardly-oblique angle from said first center.

58. A fixture for securing a surgical handpiece against rotation during a torquing procedure, said fixture comprising:
- a first body member defining a handpiece-receiving opening extending transversely therethrough and structurally adapted for receiving a surgical handpiece therein,
- said body member including a body member outer surface and a securing means for securing in said handpiece-receiving opening the surgical handpiece against rotation during a torquing procedure,
- said securing means including said body member defining a key slot communicating said body member outer surface with said handpiece-receiving opening,
- a second body member attached to said first body member,
- said second body member defining a lower surface, a left end surface, and a sloped upper surface which merges into said left end surface,
- said first body member defining a right end surface having a height greater than the height of said left end surface, and a horizontal upper surface merging into said right end surface, and
- said surfaces being proportioned to be held conveniently in the hand of the user.

59. An apparatus for assembling and/or disassembling an acoustic member to and/or from a surgical handpiece, said apparatus comprising:
- a body member including a defining means for defining a handpiece-receiving opening extending transversely therethrough for receiving a surgical handpiece therein,
- said body member including a securing means for securing the surgical handpiece in position in said handpiece-receiving opening,
- said body member having a first end and a second end, and
- said body member further including at said first end a first body portion through which said handpiece-receiving opening passes, and an elongated second body portion attached and adjacent to said first body portion and tapering so as to be thinner at said second end than at said second body portion adjacent to said first body portion.

60. An apparatus for assembling or disassembling an acoustic member to or from a surgical handpiece, said apparatus comprising:
- a body member including a defining means for defining a handpiece-receiving opening extending transversely therethrough for receiving a surgical handpiece therein,
- said body member including a securing means for securing the surgical handpiece in position in said handpiece-receiving opening, and
- said handpiece-receiving opening having a periphery which is defined by four successively contiguous arcs consisting of a first and third arc bracketing a common first center point; a second arc contiguous with the first and third arcs and having a second center point spaced from the first center point of said first and third arcs; and a fourth arc contiguous with the third and first arcs but having a third center point spaced from the first and second center points.

61. The apparatus of claim 60 including,
- said second center being spaced horizontally from said first center, and
- said third center being at an upwardly-oblique angle from said first center.

* * * * *